United States Patent
Mandziy et al.

(10) Patent No.: US 8,866,490 B1
(45) Date of Patent: Oct. 21, 2014

(54) METHOD AND APPARATUS FOR ELIMINATING TAIL EFFECT IN TOUCH APPLICATIONS

(71) Applicant: Cypress Semiconductor Corporation, San Jose, CA (US)

(72) Inventors: Vasyl Mandziy, Lviv (UA); Igor Kolych, Lviv (UA); Volodymyr Hutnyk, Lviv (UA); David G. Wright, San Diego, CA (US)

(73) Assignee: Cypress Semiconductor Corporation, San Jose, CA (US)

( * ) Notice: Subject to any disclaimer, the term of this patent is extended or adjusted under 35 U.S.C. 154(b) by 0 days.

(21) Appl. No.: 13/800,468

(22) Filed: Mar. 13, 2013

Related U.S. Application Data

(60) Provisional application No. 61/754,028, filed on Jan. 18, 2013.

(51) Int. Cl.
  *G01R 35/00* (2006.01)
  *G01R 27/26* (2006.01)
  *G06F 3/041* (2006.01)
  *G01N 27/22* (2006.01)

(52) U.S. Cl.
  CPC .......... *G01R 35/005* (2013.01); *G01R 27/2605* (2013.01); *G01N 27/22* (2013.01); *G06F 3/0418* (2013.01)
  USPC ........... 324/601; 324/663; 324/687; 345/173; 345/174

(58) Field of Classification Search
  CPC .. G01R 27/2605; G01R 27/223; G01R 35/00; G06F 3/0488; G06F 3/044; G06F 3/0418; G01N 27/22
  USPC ................... 324/663, 687, 601; 345/173, 174
  See application file for complete search history.

(56) References Cited

U.S. PATENT DOCUMENTS

| | | |
|---|---|---|
| 4,707,845 A | 11/1987 | Krein et al. |
| 7,499,039 B2 | 3/2009 | Roberts |
| 7,821,425 B2 | 10/2010 | Philipp |
| 8,294,687 B1 | 10/2012 | Ksondzyk |

(Continued)

FOREIGN PATENT DOCUMENTS

WO 2012176639 A 12/2012

OTHER PUBLICATIONS

Fischer, Dirk, "Capacitive Touch Sensors: Application Fields, Technology Overview, and Implementation Example", Fujitsu Microelectronics Europe; Langen, Germany; v4, dated Jan. 12, 2010; 12 pages.

(Continued)

*Primary Examiner* — Amy He

(57) ABSTRACT

Techniques for eliminating tail effect are described herein. In an example embodiment, a device comprises a sensor coupled with a processing logic. The sensor is configured to measure a plurality of measurements from a sensor array when the sensor array is in an unsettled state, where the measurements represent a conductive object that is proximate to a touch-sensing surface of the sensor array. The processing logic is configured to determine a set of adjustment values that correspond to a tail effect associated with the plurality of measurements, and to generate adjusted measurements corresponding to the plurality of measurements based on the set of adjustment values.

20 Claims, 9 Drawing Sheets

(56) References Cited

U.S. PATENT DOCUMENTS

| | | | |
|---|---|---|---|
| 8,300,019 B2 * | 10/2012 | Elias et al. | 345/173 |
| 2003/0210235 A1 | 11/2003 | Roberts | |
| 2006/0227115 A1 | 10/2006 | Fry | |
| 2007/0074913 A1 * | 4/2007 | Geaghan et al. | 178/18.06 |
| 2009/0314621 A1 | 12/2009 | Hotelling | |
| 2010/0013800 A1 | 1/2010 | Elias et al. | |
| 2010/0079401 A1 | 4/2010 | Staton | |
| 2010/0321331 A1 | 12/2010 | Oda et al. | |
| 2011/0148785 A1 | 6/2011 | Oda et al. | |
| 2011/0170099 A1 | 7/2011 | Ko | |
| 2012/0050180 A1 * | 3/2012 | King et al. | 345/173 |
| 2012/0098783 A1 | 4/2012 | Badaye et al. | |
| 2012/0162144 A1 | 6/2012 | Faahraeus et al. | |
| 2012/0182251 A1 | 7/2012 | Krah | |
| 2012/0200530 A1 | 8/2012 | Wu et al. | |
| 2013/0069905 A1 | 3/2013 | Krah et al. | |
| 2013/0187704 A1 | 7/2013 | Edwards | |
| 2014/0192027 A1 | 7/2014 | Ksondzyk et al. | |

OTHER PUBLICATIONS

International Search Report for International Application No. PCT/US13/62331 dated Feb. 12, 2014; 2 pages.
USPTO Advisory Action for U.S. Appl. No. 14/038,423 dated Jul. 25, 2014; 2 pages.
USPTO Final Rejection for U.S. Appl. No. 14/038,423 dated May 22, 2014; 11 pages.
USPTO Non-Final Rejection for U.S. Appl. No. 14/038,423 dated Jan. 14, 2014; 9 pages.
Written Opinion of the International Searching Authority for International Application No. PCT/US13/62331 dated Feb. 12, 2014; 4 pages.
Wu, Xiaoling et al., "Touchware: A Software-Based Technique for High-Resolution Multi-Touch Sensing Devices," Int. J. Ad Hoc and Ubiquitous Computing, vol. X, No. X, 200x; 13 pages.
USPTO Notice of Allowance for U.S. Appl. No. 14/038,423 dated Sep. 9, 2014; 9 pages.

* cited by examiner

| TX Index \ RX | 0 | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|
| 0 | 0 | -1 | -1 | -1 | -1 | -1 | -1 | -1 | -1 | -1 | -1 | -1 | -1 | -1 | -1 | -1 | -1 | -1 | -1 | -1 | -1 |
| 1 | 0 | -3 | -3 | -2 | -1 | -1 | -3 | -1 | -1 | -1 | -1 | -3 | -2 | -1 | -2 | 0 | -1 | 0 | 0 | -1 | 0 |
| 2 | 0 | -1 | 0 | 0 | 1 | 0 | 0 | 0 | 1 | 0 | -1 | 0 | -1 | 0 | -2 | 61 | 89 | 86 | 46 | 94 | 84 |
| 3 | 0 | -1 | 0 | 0 | 1 | -2 | 1 | 0 | 0 | 0 | 0 | -3 | -3 | -1 | -2 | 123 | 113 | 105 | 92 | 107 | 134 |
| 4 | -1 | -3 | 3 | 0 | -2 | 2 | 4 | -3 | 0 | 0 | 0 | 0 | -4 | 0 | 102 | 124 | 113 | 109 | 106 | 124 | 73 |
| 5 | -1 | -1 | 1 | -1 | 0 | 3 | -1 | -2 | 0 | 0 | 6 | -2 | -3 | -1 | 143 | 124 | 116 | 103 | 99 | 107 | 52 |
| 6 | -2 | -3 | 0 | -1 | 0 | -1 | -2 | 0 | -1 | -2 | -5 | 5 | -3 | 57 | 145 | 124 | 105 | 98 | 93 | 106 | -2 |
| 7 | 0 | -1 | 0 | -1 | 0 | 1 | 0 | 1 | 1 | 2 | -1 | -2 | -1 | 91 | 129 | 116 | 120 | 114 | 108 | 59 | -2 |
| 8 | 1 | -3 | -2 | 0 | 1 | 1 | -1 | -1 | 2 | 0 | -1 | 0 | -1 | 41 | 76 | 121 | 114 | 126 | 113 | 5 | 0 |
| 9 | 0 | -3 | -4 | -3 | -1 | -1 | -1 | -1 | -2 | -1 | -2 | -2 | -1 | -1 | 0 | 55 | 0 | 0 | 9 | 5 | 0 |
| 10 | 0 | 0 | 0 | 0 | 0 | 0 | 0 | 0 | 0 | 0 | 0 | 0 | 0 | 0 | 0 | 5 | 0 | 0 | 0 | 0 | 0 |

620 Adjusted Contact

METHOD AND APPARATUS FOR ELIMINATING TAIL EFFECT IN TOUCH APPLICATIONS

PRIORITY

This application claims the priority and benefit of U.S. Provisional Application No. 61/754,028, filed on Jan. 18, 2013, the entire contents of which are incorporated by reference herein.

TECHNICAL FIELD

This disclosure generally relates to the field of touch-sensor devices and, in particular, to processing of touch sensor data.

BACKGROUND

Computing devices, such as notebook computers, personal digital assistants, mobile communication devices, portable entertainment devices (e.g., handheld video games, multimedia players, etc.), and set-top-boxes (e.g., digital cable boxes, digital video disc (DVD) players, etc.) may include user interface devices that facilitate interaction between a user and the computing device. One type of user interface device that has become common is a touch-sensor device or touch input device that operates by way of capacitance sensing. A touch-sensor device may be in the form of a touchscreen, touch-sensor pad, touch-sensor slider, or touch-sensor buttons, and may include a sensor comprising an array of capacitive sensor elements. Capacitive sensing typically involves scan operations that periodically measure changes in capacitance associated with the capacitive sensor elements to determine a presence, position, and/or movement of a conductive object (e.g., a stylus, a user's finger, etc.) relative to a touch input device.

To achieve sufficient accuracy, capacitive sensing scan operations typically require a sensor to settle between consecutive measurements. However, this requirement limits the functionality of the touch input device and/or leads to poor user experience.

BRIEF DESCRIPTION OF THE DRAWINGS

FIG. 3A is a block diagram illustrating a tail effect according to an example embodiment.

FIG. 6A is a block diagram illustrating experimental results of a tail effect according to an example embodiment.

FIG. 6B is a block diagram illustrating experimental results of eliminating the tail effect of FIG. 6A according to an example embodiment.

DETAILED DESCRIPTION

Figure 1:
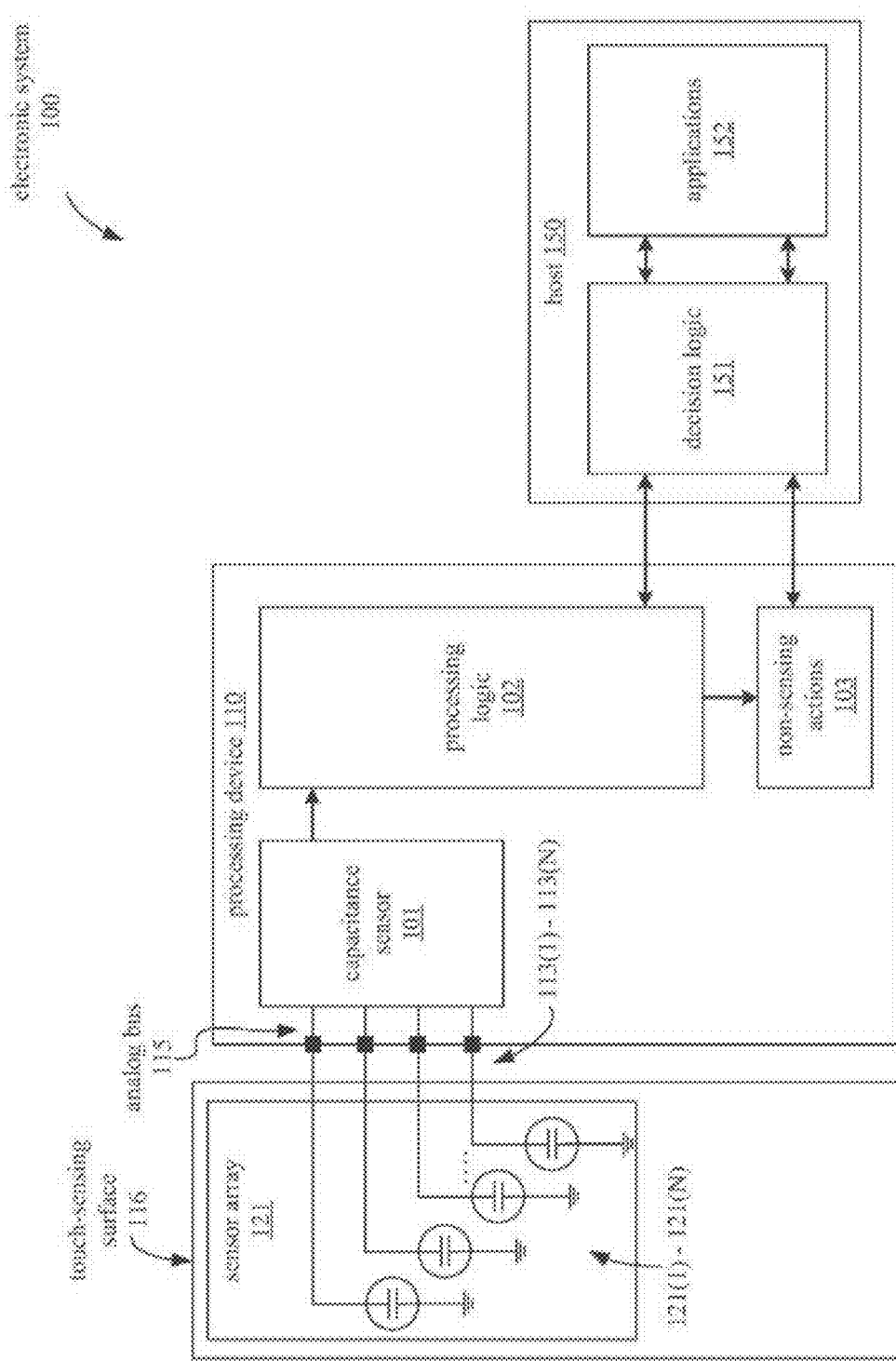
FIG. 1 is a block diagram illustrating an embodiment of an example electronic system that includes touch sensor components.

The following description sets forth numerous specific details such as examples of specific systems, components, methods, and so forth, in order to provide a good understanding of various embodiments of the techniques described herein for eliminating tail effects in touch applications. It will be apparent to one skilled in the art, however, that at least some embodiments may be practiced without these specific details. In other instances, well-known components or methods are not described in detail or are presented in a simple block diagram format in order to avoid unnecessarily obscuring the techniques described herein. Thus, the specific details set forth hereinafter are merely exemplary. Particular implementations may vary from these exemplary details and still be contemplated to be within the spirit and scope of the present invention.

Overview

Described herein are various embodiments of techniques for eliminating tail effects in touch applications. As used herein, "tail effect" refers to a parasitic signal increase (or a parasitic signal decrease) in one or more sensor elements of a sensor array. In some embodiments, the tail effect is extended along one or more rows or columns of sensor elements in the sensor array, rather than being localized to sensor elements directly affected by a contact of a conductive object with the touch-surface of the sensor array. As used herein, "contact" refers to a physical touch of a conductive object (e.g., a stylus, a user's finger, and the like) on the touch-surface of the sensor array and/or to a hover in which the conductive object is sufficiently proximate to affect the sensor elements without being in physical touch with the touch-surface of the sensor array.

In one example embodiment, a device comprises a sensor coupled with a processing logic. The sensor is configured to measure a plurality of measurements from a sensor array when the sensor array is in an unsettled state, where the measurements are affected by a conductive object proximate to a touch-sensing surface of the sensor array. The processing logic is configured to determine a set of adjustment values that correspond to a tail effect associated with the plurality of measurements, and to generate adjusted measurements corresponding to the plurality of measurements based on the set of adjustment values. In some aspects of this embodiment, the processing logic may be further configured to determine location coordinates on the touch-sensing surface for the conductive object based on the adjusted measurements and/or to track movement of the conductive object on the touch-sensing surface based on the adjusted measurements.

In another example embodiment, a method for eliminating tail effects comprises the steps of: receiving a plurality of measurements that are measured from a sensor array when the sensor array is in unsettled state, where the measurements are affected by a conductive object proximate to the sensor array; determining a set of adjustment values that correspond to a tail effect associated with the plurality of measurements; and generating adjusted measurements corresponding to the plurality of measurements based on the set of adjustment values. In some aspects of this embodiment, the plurality of measurements may include signal values for sensor elements formed by a particular receive electrode of the sensor array, and determining the adjusted measurements comprises the steps of: computing a sum of indices of transmit electrodes that form the sensor elements along the particular receive electrode; computing a sum of the signal values for the sensor elements; computing a parameter value based on the sum of indices and the sum of the signal values; and adjusting each signal value, to obtain a corresponding adjusted measurement, based at least on the parameter value, the signal value itself, and the index of the transmit electrode corresponding to the signal value.

In another example embodiment, a system comprises a capacitive sensor array coupled with a capacitive sensor and a processing logic coupled with the capacitive sensor. The capacitive sensor array comprises a plurality of sensor elements. The capacitive sensor is configured to measure a plurality of measurements from the sensor elements when the sensor array is in unsettled state, where the measurements are affected by a conductive object proximate to the capacitive sensor array. The processing logic is configured to determine a set of adjustment values that correspond to a tail effect associated with the conductive object, and to generate adjusted measurements corresponding to the plurality of measurements based on the set of adjustment values.

Example Operational Context

FIG. 1 illustrates a block diagram of one example embodiment of an electronic system 100 including a processing device 110 that may be configured to measure capacitances from a touch-sensing surface and to generate adjustments to compensate for, and/or eliminate, tail effects. The electronic system 100 includes a touch-sensing surface 116 (e.g., a touchscreen, a touch pad, or the like) coupled to the processing device 110 and a host 150. In some embodiments, the touch-sensing surface 116 is a two-dimensional user interface that uses a sensor array 121 to detect touches on the surface 116.

In the example embodiment of FIG. 1, the sensor array 121 includes sensor elements 121(1)-121(N) (where N is a positive integer) that are disposed as a two-dimensional matrix (also referred to as an XY matrix). The sensor array 121 is coupled to pins 113(1)-113(N) of the processing device 110 via one or more analog buses 115 transporting multiple signals. In this embodiment, each sensor element 121(1)-121(N) is represented as a capacitor. The self capacitance of each sensor element in the sensor array 121 is measured by a capacitance sensor 101 in the processing device 110. Depending on the type of sensor array, in some embodiments the capacitance sensor may be configured to detect the mutual capacitance of a sensor element when a conductive object (e.g., stylus, user's finger, etc.) is in contact with the sensor element.

Capacitance sensor 101 may include a relaxation oscillator or other means to convert a capacitance into a measured value. Capacitance sensor 101 may also include a counter or timer to measure the oscillator output. The capacitance sensor 101 may further include software components to convert the count value (e.g., capacitance value) into a sensor element detection decision (also referred to as switch detection decision) or relative magnitude. In some embodiments, the measured value obtained by capacitance sensor 101 may be a signal value that represents one or more characteristics of a signal; in addition, or instead of, in some embodiments a signal value may be a value that is derived from the measured value based on a signal characteristic, e.g., such as voltage and/or current magnitude, raw capacitance, and the like. It should be noted that there are various known methods for measuring capacitance, such as current versus voltage phase shift measurement, resistor-capacitor charge timing, capacitive bridge divider, charge transfer, successive approximation, sigma-delta modulators, charge-accumulation circuits, field effect, mutual capacitance, frequency shift, or other capacitance measurement algorithms. It should also be noted that instead of evaluating the raw counts relative to a threshold, a capacitance sensor may be evaluating other measurements to determine the user interaction. For example, in a capacitance sensor having a sigma-delta modulator, the capacitance sensor may be evaluating the ratio of pulse widths of the output, instead of the raw counts being over or under a certain threshold.

In the example embodiment of FIG. 1, processing device 110 further includes processing logic 102. Operations of processing logic 102 may be implemented in firmware; alternatively, they may be implemented in hardware or software. Processing logic 102 is configured to perform operations that implement the techniques for eliminating tail effects as described herein. For example, processing logic 102 may receive measurements from capacitance sensor 101, adjust the measurements to compensate/eliminate tail effects, and then use the adjusted measurements to determine the state of the sensor array 121, such as whether an object (e.g., a finger, a stylus, or the like) is detected on or in proximity to the sensor array 121 (e.g., determining the presence of the object), where the object is detected on the sensor array (e.g., determining the location of the object), tracking the motion of the object, or other information related to an object detected at the sensor array.

In another embodiment, instead of performing the operations of the processing logic in a processing device (e.g., such as processing device 110), the processing device may send the raw data or partially-processed data to a host, e.g., such as host 150. As illustrated in FIG. 1, host 150 may include decision logic 151 that performs some or all of the operations described above for processing logic 102. Operations of decision logic 151 may be implemented in firmware, hardware, software, or a combination thereof. Host 150 may include a high-level Application Programming Interface (API) in applications 152 that perform routines on the received data, such as compensating for sensitivity differences, other compensation algorithms, baseline update routines, start-up and/or initialization routines, interpolation operations, scaling operations and/or operations that implement the techniques for eliminating tail effects as described herein. The operations described with respect to the processing logic 102 may be implemented in the decision logic 151, the applications 152, or in other hardware, software, and/or firmware external to the processing device 110. In some other embodiments, the processing device 110 is the host 150.

In another embodiment, processing device 110 may also include a non-sensing actions block 103. This block 103 may be used to process and/or receive/transmit data to and from the host 150. For example, additional components may be implemented to operate with the processing device 110 along with the sensor array 121 (e.g., keyboard, keypad, mouse, trackball, LEDs, displays, or other peripheral devices).

Processing device 110 may reside on a common carrier substrate such as, for example, an integrated circuit (IC) die substrate, or a multi-chip module substrate. Alternatively, the components of the processing device 110 may be one or more separate integrated circuits and/or discrete components. In one embodiment, processing device 110 may be a programmable system on a chip such as, for example, the Programmable System on a Chip (PSoC™) processing device, developed by Cypress Semiconductor Corporation, San Jose, Calif. Alternatively, processing device 110 may be one or more other processing devices known by those of ordinary skill in the art, such as a microprocessor or central processing unit, a controller, special-purpose processor, digital signal processor (DSP), an application specific integrated circuit (ASIC), a field programmable gate array (FPGA), or other programmable device. In an alternative embodiment, for example, processing device 110 may be a network processor having multiple processors including a core unit and multiple micro-engines. Additionally, processing device 110 may include any combination of general-purpose processing device(s) and special-purpose processing device(s).

In one embodiment, electronic system 100 is implemented in a device that includes touch-sensing surface 116 as the user interface, such as handheld electronics, portable and/or smart telephones, cellular telephones, notebook computers, personal computers, personal data assistants (PDAs), kiosks, keyboards, televisions, remote controls, monitors, handheld multi-media devices, handheld video players, gaming devices, control panels of a household or industrial appliances, or other computer peripheral or input devices. Alternatively, electronic system 100 may be used in other types of devices. It should be noted that the components of electronic system 100 may include all the components described above. Alternatively, electronic system 100 may include only some of the components described above, or include additional components not listed herein.

Figure 2:
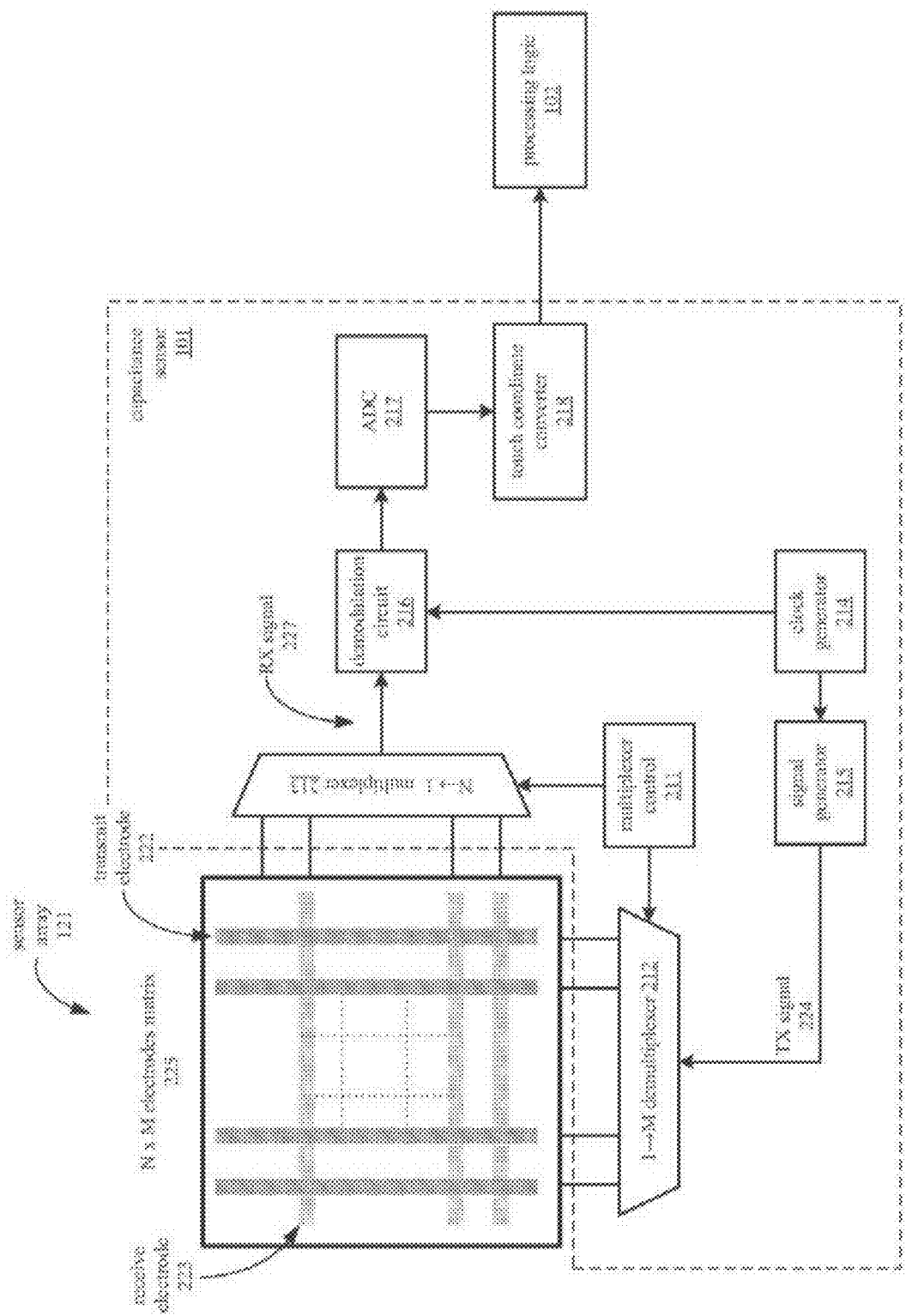
FIG. 2 is a block diagram illustrating an embodiment of an example sensor system that processes touch sensor data.

FIG. 2 is a block diagram illustrating one embodiment of a capacitive touch sensor array 121 and a capacitance sensor 101 that converts measured capacitances to coordinates. The coordinates are calculated based on measured capacitances. In one embodiment, sensor array 121 and capacitance sensor 101 are implemented in a system such as electronic system 100. Sensor array 121 includes a matrix 225 of N×M electrodes having N receive electrodes and M transmit electrodes. For example, matrix 225 includes transmit (TX) electrode 222 and receive (RX) electrode 223. Each of the electrodes in matrix 225 is connected with capacitance sensing circuit 201 through demultiplexer 212 and multiplexer 213.

Capacitance sensor 101 includes multiplexer control 211, demultiplexer 212 and multiplexer 213, clock generator 214, signal generator 215, demodulation circuit 216, and analog to digital converter (ADC) 217. ADC 217 is further coupled with touch coordinate converter 218. Touch coordinate converter 218 outputs a signal to processing logic 102.

The transmit and receive electrodes in matrix 225 may be arranged so that each of the transmit electrodes overlap and cross each of the receive electrodes such as to form an array of sensor elements at the intersections, while maintaining galvanic isolation from each other. Thus, each transmit electrode may be capacitively coupled with each of the receive electrodes. For example, transmit electrode 222 is capacitively coupled with receive electrode 223 at the point where transmit electrode 222 and receive electrode 223 overlap.

In some embodiments (not shown), a capacitance sensor (e.g., such as sensor 101 in FIG. 1) may be configured to use mutual capacitance sensing technique according to which a mutual capacitance present at the intersection of two electrodes can be measured by a processing device (e.g., such as processing device 120 in FIG. 1). The change in this mutual capacitance at one or more intersections allows a processing logic to determine the location of a contact on the sensor array. With mutual capacitance sensing, one set of electrodes (e.g., such as the column electrodes) are designated as transmit (TX) electrodes. The transmit electrodes are driven with a TX signal that is applied to the transmit electrodes by a transmit multiplexer. Another set of electrodes (e.g., such as the row electrodes) are designated as receive (RX) electrodes. The mutual capacitance of the sensor elements formed at the intersections of the rows and columns may be measured by sampling a signal on each of the receive electrodes. In some embodiments, a receive multiplexer may be used to sample the signal on one or more of the receive electrodes and to provide the receive measurement signal back to the processing logic 102 (and/or to another component of the processing device).

Referring back to FIG. 2, clock generator 214 supplies a clock signal to signal generator 215, which produces a TX signal 224 to be supplied to the transmit electrodes of touch sensor 121. In one embodiment, signal generator 215 includes a set of switches that operate according to the clock signal from clock generator 214. The switches may generate a TX signal 224 by periodically connecting the output of signal generator 215 to a first voltage and then to a second voltage, where said first and second voltages are different.

The output of signal generator 215 is connected with demultiplexer 212, which allows a TX signal 224 to be applied to any of the M transmit electrodes of touch sensor 121. In one embodiment, multiplexer control 211 controls demultiplexer 212 so that the TX signal 224 is applied to each transmit electrode 222 in a controlled sequence. Demultiplexer 212 may also be used to ground, float, or connect an alternate signal to the other transmit electrodes to which the TX signal 224 is not currently being applied.

Because of the capacitive coupling between the transmit electrodes and the receive electrodes, a TX signal 224 applied to each transmit electrode induces a current within each of the receive electrodes. For instance, when the TX signal 224 is applied to transmit electrode 222 through demultiplexer 212, the TX signal 224 induces a receive (RX) signal 227 on the receive electrodes in matrix 225. The RX signal 227 on each of the receive electrodes can then be measured in sequence by using multiplexer 213 to connect each of the N receive electrodes to demodulation circuit 216 in sequence.

The mutual capacitance associated with each intersection between a TX electrode and an RX electrode can be sensed by selecting every available combination of TX electrode and an RX electrode using demultiplexer 212 and multiplexer 213. To improve performance, multiplexer 213 may also be segmented to allow more than one of the receive electrodes in matrix 225 to be routed to additional demodulation circuits 216. In an optimized configuration, where there is a 1-to-1 correspondence of instances of demodulation circuit 216 with receive electrodes, multiplexer 213 may not be present in the system.

When an object, such as a finger, approaches electrode matrix 225, the object causes a decrease in the mutual capacitance between only some of the electrodes. For example, if a finger is placed near the intersection of transmit electrode 222 and receive electrode 223, the presence of the finger will decrease the mutual capacitance between electrodes 222 and 223. Thus, the location of the finger on the touchpad can be determined by identifying the one or more receive electrodes having a decreased mutual capacitance in addition to identifying the transmit electrode to which the TX signal 224 was applied at the time the decreased mutual capacitance was measured on the one or more receive electrodes.

By determining the mutual capacitances associated with each intersection of electrodes in the matrix 225, the locations of one or more touch contacts may be determined. The determination may be sequential, in parallel, or may occur more frequently at commonly used electrodes.

In some embodiments, other methods for detecting the presence of a finger or conductive object may be used where the finger or conductive object causes an increase in capacitance at one or more electrodes, which may be arranged in a grid or other pattern. For example, a finger placed near an electrode of a capacitive sensor may introduce an additional capacitance to ground that increases the total capacitance between the electrode and ground. The location of the finger can be determined from the locations of one or more electrodes at which an increased capacitance is detected.

The induced current signal 227 is rectified by demodulation circuit 216. The rectified current output by demodulation circuit 216 can then be filtered and converted to a digital code by ADC 217.

The digital code may then be converted to touch coordinates indicating a position of an input on touch sensor array 121 by touch coordinate converter 218. The touch coordinates are transmitted as an input signal to processing logic 102. In one embodiment, the input signal is received at an input to processing logic 102. In one embodiment, the input may be configured to receive capacitance measurements indicating a plurality of row coordinates and a plurality of column coordinates. Alternatively, the input may be configured to receive row coordinates and column coordinates.

In some embodiments, processing logic 102 may be configured to generate (or to receive, e.g., from touch coordinate receiver 218) capacitance measurements that represent diff signals (also referred to herein as "diff signal values"). For example, processing logic 102 may be configured to determine a diff signal for a given sensor element as the difference between the settled (e.g., expected or fully charged) capacitance of a sensor element (e.g., when a conductive object is not in contact with the sensor array and the sensor array is not being scanned) and the capacitance of the sensor element that is measured as part of a scan operation (e.g., when a conductive object may or may not be in contact with the sensor array). The capacitance used to compute a diff signal for a sensor element may be a self-capacitance and/or a mutual capacitance of the sensor element.

In various embodiments, the processing logic may compute the diff signals for each of the sensor elements in a sensor array based on capacitance measurements that represent the self-capacitances and/or the mutual capacitances of the sensor elements. For example, a self-capacitance of a given sensor element may include a capacitance formed between the sensor element and a reference voltage (e.g., such as ground). A mutual capacitance of a given sensor element may include a capacitance formed between the electrodes that form the sensor element and/or one or more conductive objects (e.g., such as a stylus or user's finger) that are electrically insulated from the capacitive sensor element.

Tail Effect

Figure 3A:
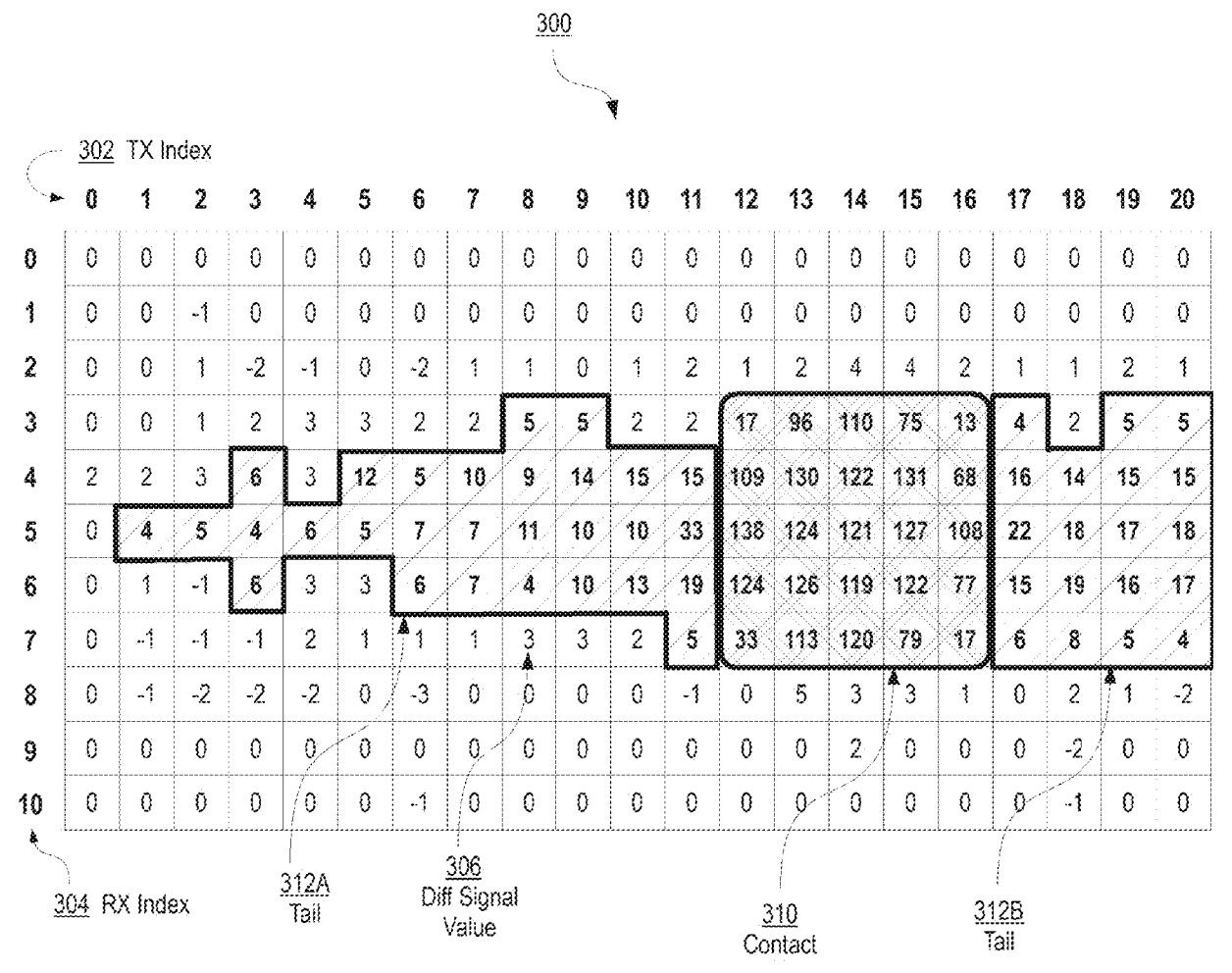

Depending on the particular design and construction of a sensor array, the tail effect may be a parasitic signal increase or a parasitic signal decrease in one or more sensor elements of the sensor array that are affected by a contact with a conductive object (e.g., a stylus, a user's finger, etc.) In some embodiments, the tail effect may extend to sensor elements that are positioned along one or more rows (or one or more columns) from the location where an object is in contact with the sensor array, rather than being localized to sensor elements directly affected by the contact. FIG. 3A is a block diagram illustrating a tail effect according to an example embodiment.

FIG. 3A illustrates a logical diagram of a sensor array 300, where the sensor elements of the sensor array are represented as boxes at the intersections of 21 transmit electrodes and 11 receive electrodes. A sensor or processing logic (not shown) that operates sensor array 300 stores/associates a separate index value for each separate transmit electrode, where the index values are arranged in a sequence representing a physical arrangement of the transmit electrodes in the sensor array; similarly, the sensor or processing logic also stores/associates a separate index value for each separate receive electrode, where the index values are arranged in a sequence representing a physical arrangement of the receive electrodes in the sensor array. Using the embodiment in FIG. 3A as an example, TX index 302 is a sequence of integer values ranging from 0 to 20 that represent the 21 transmit electrodes; similarly, RX index 304 is a sequence of integer values ranging from 0 to 10 that represent the 11 receive electrodes. FIG. 3A also illustrates the diff signals, obtained by a given scan operation at a given point in time, for each of the sensor elements in sensor array 300. For example, diff signal 306 (having a value of "3") is measured or otherwise obtained for the sensor element located at the intersection of the transmit electrode with TX index of "8" and the receive electrode with RX index of "7". It is noted that since various embodiments may use sensor arrays with various numbers of transmit and receive electrodes and various numbering schemes for the corresponding TX and RX indexes, the techniques for eliminating tail effect described herein are not limited to any particular number of electrodes or to any particular indexing scheme. Thus, the sensor array and its TX and RX indexes depicted in FIG. 3A are to be regarded in an illustrative rather than a restrictive sense.

In FIG. 3A, the diff values for the sensor elements of sensor array 300 are obtained by a scan operation at a given point in time. The diff values indicate that a contact 310 is present on the touch-surface of the sensor array. The diff values also indicate, however, that tail effects are also present as illustrated by tail 312A and tail 312B. It is noted that the diff values represent the state of the sensor elements of the sensor array at the time the scan operation is performed—thus, the contact illustrated in FIG. 3A may be a stationary contact (e.g., such as a tap) or may be part of a more complex gesture (e.g., such as a scrolling gesture).

In some embodiments, it was determined that the tail effect is caused by the frequency of sensor recharging, which is also referred to hereinafter as "TX frequency." For example, depending on the type of sensor elements in the sensor array, the TX frequency may be the frequency of TX electrode potential variation or the frequency of mutual capacitance recharging. In a scan operation, the sensor applies signals to the transmit electrodes over connection lines (e.g., such as metal traces, pins, vias, and the like) that connect the sensor array to the sensor, thereby recharging the sensor elements. For example, a module in the sensor may apply a voltage or current to one or more of the transmit electrodes, thereby causing a capacitance to be formed at the intersections (e.g., sensor elements) with the receive electrodes. (It is noted that applying the voltage or current to the transmit electrodes is also referred to as "driving" the sensor elements.) The same (or a different) sensor module then measures the self-capacitance and/or the mutual capacitance of the sensor elements in the entire sensor array (or in a portion thereof).

As discussed above, it was determined that a sub-optimal TX frequency causes tail effect in some embodiments. A denomination of "tau" may be used to represent the length of time an individual sensor element needs to fully settle to its expected charge, where the value of tau is specific to each sensor array as it is defined by the array design and the characteristics (e.g., resistance, capacitance, etc.) of the materials and components from which the sensor elements in the array are constructed. The settling time for the sensor array as a whole may be expressed as multiples of tau (e.g., such as 3tau, 4tau, etc.), and this characteristic defines the TX frequency for the sensor array.

In practical operation, it is desirable to drive a sensor array at a higher frequency in order to obtain faster response times without sacrificing accuracy. Thus, a TX frequency is considered to be optimal when the sensor array (and, respectively, its sensor elements) is allowed sufficient time to settle between scan operations while still providing acceptably good measurements. For example, in some embodiments such sufficient settling time may be set at 95% of the full settling time of the sensor array, and such sufficient settling time may be represented as 3tau. In one particular embodiment, experiments have shown that less than 5% of tail effect signal provides sufficiently good measurements from a sensor array (e.g., for the purpose of finger tracking). However, in this particular embodiment, 250 kHz is the fastest TX frequency that can be used to obtain less than 5% tail effect signal, which frequency is considerably lower than the optimal TX frequency of 350 kHz that is determined at 3tau settling time for this particular sensor array. In other words, in this particular embodiment the tail effect requires the sensor to drive the sensor array at a sub-optimal TX frequency (with settling time that is greater than 3tau) in order to achieve acceptably good measurements (e.g., for the purpose of tracking an object, such as a user's finger, across the sensor array). Thus, as used herein, an "unsettled state" refers to a state in which a sensor array is being driven at a sub-optimal TX frequency; a sensor array is referred to as being "unsettled" when the sensor array is in an unsettled state.

One reason that necessitates the use of sub-optimal TX frequencies is that a contact by a conductive object (e.g., such as a finger touch) adds capacitance to the RC time constant of the sensor array. Depending on how much settling time the sensor array is given (e.g., by tuning the TX frequency) the tail effect can be small or large. For example, if the TX frequency is tuned to allow 90% settling without a contact, and a finger touch causes a reduction to 88% settling, this means that 2% of the total capacitance charge will be lost to the tail effect, thereby leading to less accurate measurements. This tail effect is parasitic in nature because, as illustrated in FIG. 3A, an entire row/column of sensor elements is affected rather than just sensor elements around the location of the contact.

It is noted that various different sensor designs are prone to the parasitic tail effect described above, except that the degree to which the tail effect is exhibited may vary from design to design. Thus, in various embodiments, the techniques for eliminating tail effect described herein may be implemented for sensor arrays that were constructed according to various different design technologies. Such designs and technologies include, but are not limited to, single-solid-diamond design, MH3, and metal mesh.

Examples of Processing Tail Effect Data

As illustrated in FIG. 3A, the diff signals in tails 312A and 312B increase from the left side to the right side of sensor array 300 and are neglible near the left side. This is because in the embodiment of FIG. 3A, the TX frequency near the left side border is optimal since the connection lines (which connect the sensor to the receive electrodes) are provided from this side of the sensor array.

In some embodiments, a curve may be used to approximate the dependence between diff signals in the tails and the index values of TX electrodes (e.g., columns). One example of such approximation can be made by a straight line:

$$S = a \cdot txIndex + b \tag{1}$$

where:
S represents a diff signal in the tail,
txIndex represents the index value of the TX electrode (as illustrated in FIG. 3A, the index values range from 0 to 20), and
a, b are some constant parameter values which define the skew (slope) and the offset (intercept) of the straight line.

In some embodiments, the a, b parameter values can be calculated using the least squares method, which is one approach to solving over-determined systems. According to the least squares method, a solution minimizes the sum of the squares of the errors made for each measurement i:

$$Q = \sum_{i=1}^{n} [S_i - (a \cdot i + b)]^2 \Rightarrow \min \tag{2}$$

The parameter values (e.g., the coefficients in Equation (2)) a, b can be computed using the following equations:

$$\begin{cases} \dfrac{\partial Q}{\partial a} = 0 \\ \dfrac{\partial Q}{\partial b} = 0 \end{cases} \tag{3}$$

Solving equations (3) yields:

$$\begin{cases} a = \dfrac{n \cdot \sum_{i=1}^{n} i \cdot S_i - \sum_{i=1}^{n} i \cdot \sum_{i=1}^{n} S_i}{n \cdot \sum_{i=1}^{n} i^2 - \left(\sum_{i=1}^{n} i\right)^2} \\ b = \dfrac{\sum_{i=1}^{n} i^2 \cdot \sum_{i=1}^{n} S_i - \sum_{i=1}^{n} i \cdot \sum_{i=1}^{n} i \cdot S_i}{n \cdot \sum_{i=1}^{n} i^2 - \left(\sum_{i=1}^{n} i\right)^2} \end{cases} \tag{4}$$

In some embodiments, the parameter values a, b are computed according to equation (4) for each particular receive electrode of a sensor array. Based on the computed parameter values, an adjustment value for each diff signal of a particular receive electrode is computed according to equation (1). Then, to completely (or at least substantially) eliminate the tail effect, the adjustment value is subtracted from its corresponding diff signal value thereby obtaining a corresponding adjusted value that is used for subsequent operations. Such subsequent operations may include, but are not limited to, determining the location coordinates of the contact on the sensor array and tracking the movement of the contact on the touch-sensing surface of the sensor array.

In some embodiments, computing the parameter values a, b according to equations (4) may be too complex. For example, in some embodiments the adjustment values for the tail effect must be computed in firmware within a very limited time frame (e.g., between two consecutive scan operations or between two consecutive recharges of sensor elements), and thus using equations (4) may be too computationally expensive and/or may simply take too long.

Figure 3B:
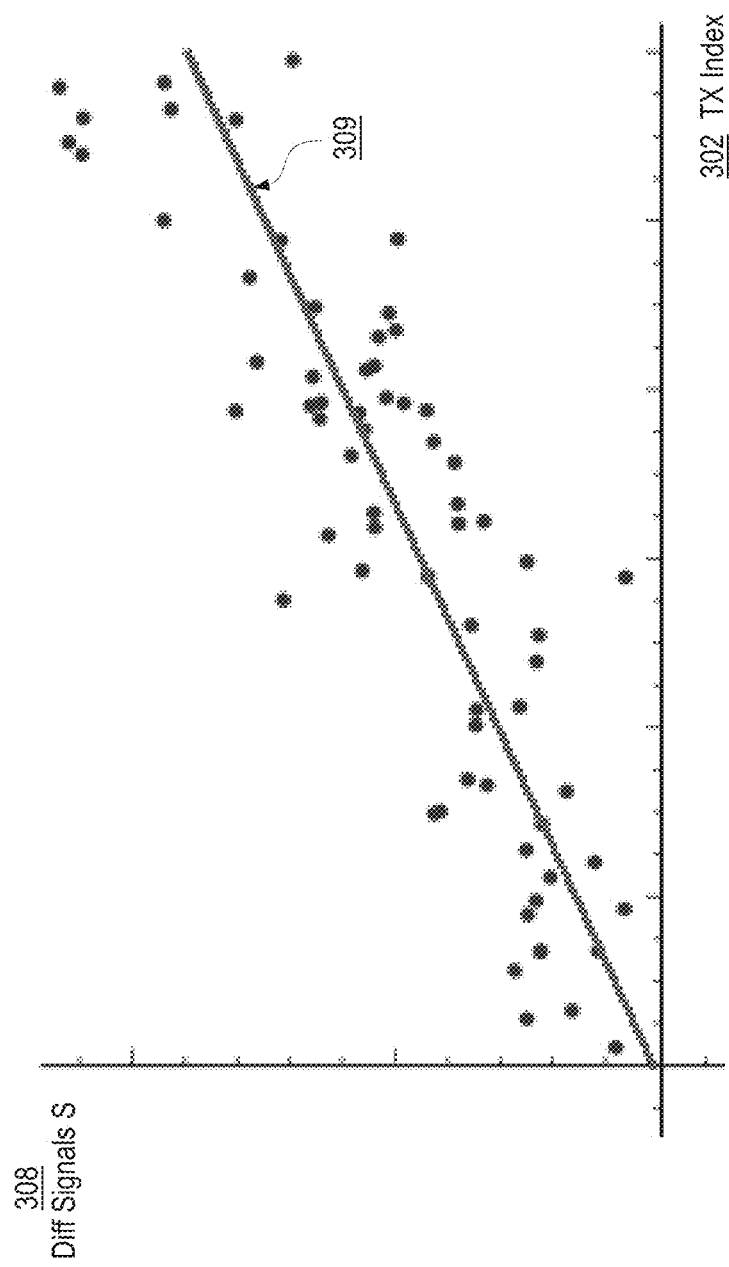
FIG. 3B is a plot illustrating an example of a simplified version of approximation by straight line to eliminate tail effect according to one embodiment.

In such embodiments, a simplified version of the approximation by straight line may be used to eliminate the tail effect. FIG. 3B illustrates a plot representing an example of such simplified approximation. In FIG. 3B, straight line 309 represents the least square approximation that fits the distribution of the diff signals 308 along their corresponding index values of TX index 302.

FIG. 3B illustrates that the parameter value b (which represents the offset, or intercept, of the approximation line 309) is close to zero because the diff signals near the left side border of the sensor array are neglible. (As discussed above, this may be because the connection lines connecting the receive electrodes to the sensor are provided from the left side border of the sensor array.) With parameter value b assumed to be 0, equation (1) transforms into:

$$S = a \cdot txIndex \quad (5)$$

Then, parameter value a can be approximately computed using the following equations:

$$\begin{cases} S_1 = a \cdot txIndex_1 \\ S_2 = a \cdot txIndex_2 \\ \ldots \\ S_n = a \cdot txIndex_n \end{cases} \quad (6)$$

Summing the left and right parts of equations (6) yields:

$$\sum_{i=1}^{n} S_i = a \cdot \sum_{i=1}^{n} txIndex_i$$

from which parameter value a can be determined as $$a = \frac{\sum_{i=1}^{n} S_i}{\sum_{i=1}^{n} txIndex_i} \quad (7)$$

Figure 5A:
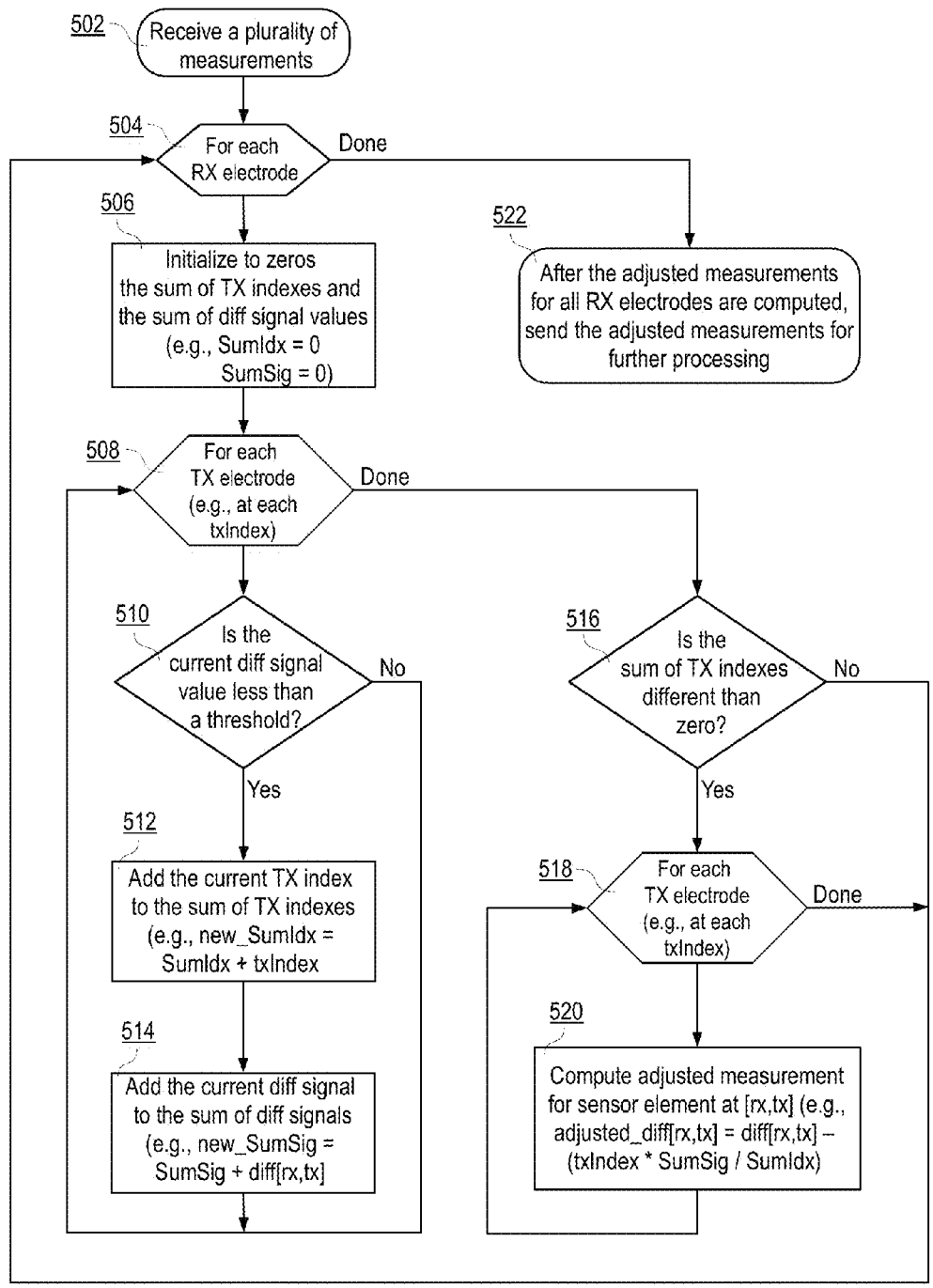
FIG. 5A illustrates a method of eliminating tail effect according to an example embodiment.

An example method using equation (7) to determine the parameter value a is illustrated in FIG. 5A below. Based on the parameter value a that is computed for a particular receive electrode, an adjustment value for each diff signal of that particular electrode is computed according to equation (5). Then, to completely (or at least substantially) eliminate the tail effect, the computed adjustment value is subtracted from its corresponding diff signal value, thereby obtaining a corresponding adjusted value that is used for subsequent operations. Such subsequent operations may include, but are not limited to, determining the location coordinates of the contact on the sensor array and tracking the movement of the contact on the touch-sensing surface of the sensor array.

Examples of Methods for Eliminating Tail Effect

Figure 4:
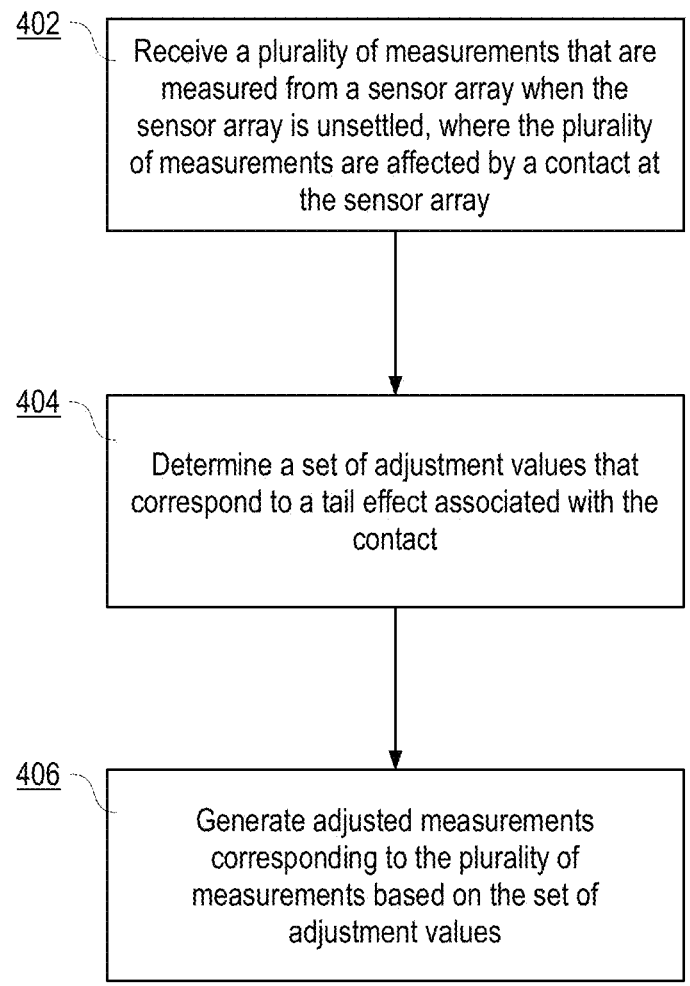
FIG. 4 illustrates an example method of eliminating tail effect according to some embodiments.

FIG. 4 illustrates an example method for eliminating tail effect. The steps of the method in FIG. 4 are described hereinafter as being performed by a processing logic (e.g., such as processing logic 102 in FIG. 1). It is noted, however, that various implementations and embodiments may use various, and possibly multiple, components to perform the operations of the method in FIG. 4. For example, in various embodiments a processing logic may be implemented in various ways including, but not limited to: as a set of stored software and/or firmware instructions which, when executed by one or more processors, are operable to perform one or more operations; as one or more software components (e.g., software modules, libraries of functions, compiled and/or interpretable object-oriented classes, dynamically linked libraries, and the like) that are executable by one or more computing devices; and as any combination(s) of one or more software components and one or more hardware components (e.g., processors, microcontrollers, Application-Specific Integrated Circuits (ASICs), and the like). In another example, in various embodiments a processing logic may be implemented in a single integrated component or its functionality may be spread across two or more components that may perform some additional operations and functionalities. Thus, the description hereinafter, of the method in FIG. 4 as being performed by a processing logic, is to be regarded in an illustrative rather than a restrictive sense.

In block 402, a processing logic receives a plurality of measurements that are measured from a sensor array when the sensor array is in an unsettled state. The measurements are affected by a contact at the touch-surface of the sensor array by a conductive object (e.g., such as a stylus or user's finger). In some embodiments, the measurements received by the processing logic may include diff signal values for all (or a portion) of the sensor elements in the sensor array; in other embodiments, the processing logic may receive raw measurements (e.g., raw capacitances) from the sensor elements and may compute the corresponding diff signal values.

Various embodiments may use various parameters to quantify the unsettled state of the sensor array during which the measurements are taken. For example, in some embodiments the sensor array may be driven at a TX frequency (e.g., the frequency at which sensor elements are recharged) that causes less than 100% settling of the array. In some embodiments, the sensor array may be driven at a TX frequency that causes array settling that is within: the range of 66% to 95% of full settling or any sub-range thereof; the range of 90% to 95% of full settling or any sub-range thereof; the range of 85% to 90% of full settling or any sub-range thereof; the range of 80% to 85% of full settling or any sub-range thereof; the range of 75% to 80% of full settling or any sub-range thereof; and the range of 66% to 75% of full settling or any sub-range thereof. In yet some other embodiments, the unsettled state of the sensor array may be defined by a sub-optimal TX frequency that is uniquely determined for the sensor array based on the tau characteristics of the array. For example, a sensor may drive an unsettled sensor array at a sub-optimal TX frequency that allows for less than 5% of tail effect signal after the tail effect adjustments have been computed and applied (e.g., as described below for blocks 404 and 406, respectively).

In some embodiments, a sensor that operates the sensor array may be configured to periodically measure, from the sensor elements, sets of measurements at a frequency of sensor element recharging that is higher than an optimal frequency that allows the sensor array to substantially settle between measurements. After measuring each set of measurements, the sensor sends each separate set to the processing logic. In turn, the processing logic performs the operations of block 402, as well as the operations in blocks 404 and 406, separately for each received set of measurements.

In some embodiments, after receiving the measurements in block 402, the processing logic may detect whether a contact is present on the sensor array. For example, the processing logic may process the received measurements against a certain metric (e.g., a threshold, a diff signal distribution spread, etc.) to determine whether a contact is detected on the sensor array. The processing logic may then proceed to adjust the received measurements for tail effect, according to blocks 404 and 406, only if a contact is detected.

In block 404, the processing logic determines a set of adjustment values that correspond to a tail effect associated with the contact at the sensor array. For example, in some embodiments, the processing logic may use an approximation model (e.g., such as the least-squares method) to fit the measurements against a certain curve, and then use the curve's parameters to determine an adjustment for each measured value. Depending on the characteristics (e.g., design, construction, etc.) of the sensor array and/or of the electronic system using the array, in various embodiments the curve may be a straight line or a line having a non-linear, but parametric curvature.

In block 406, the processing logic uses the adjustment values computed in block 404 to generate the adjusted measurements that correspond to the measurements obtained from the sensor array. For example, in some embodiments the processing logic may compute the adjusted measurements by subtracting the adjustment values from the original measurements. The adjusted measurements eliminate (or at least substantially compensate for) the tail effect that was present in the original measurements. Then, in at least some subsequent operations, the processing logic uses (and/or sends) the adjusted measurements instead, and/or in place, of the original measurements. For example, in some embodiments the processing logic or another component may use the adjusted measurements in place of the original measurements in order to determine the location coordinates of the contact on the sensor array and/or to track the movement of the contact on the touch-sensing surface of the array.

In some embodiments, the processing logic performs the operations of blocks 404 and 406 for each separate set of measurements that is read from a sensor array. In this manner, the tail effect (if present) is eliminated from the measurements obtained from the sensor array before performing any other operations that use the measurements. For example, the processing logic may perform the operations of blocks 404 and 406 between two consecutive scan operations that read measurements from a sensor array (or a portion thereof). In some embodiments, the processing logic performs the operations of blocks 404 and 406 for an initial set of measurements that are affected by a contact at a sensor array, and then performs the operations of blocks 404 and 406 for any subsequent measurements that are responsive to a subsequent movement of the contact on the touch-surface of the sensor array.

FIG. 5A illustrates an example method of eliminating tail effect that uses a simplified version of the approximation by straight line. The steps of the method in FIG. 5A are described hereinafter as being performed by a processing logic (e.g., such as processing logic 102 in FIG. 1). It is noted, however, that various implementations and embodiments may use various, and possibly multiple, components to perform the operations of the method in FIG. 5A. For example, in various embodiments a processing logic may be implemented in various ways including, but not limited to: as a set of stored software and/or firmware instructions which, when executed by one or more processors, are operable to perform one or more operations; as one or more software components that are executable by one or more computing devices; as any combination(s) of one or more software components and one or more hardware components; and as a single integrated component or as two or more components that can perform additional operations. Thus, the description hereinafter, of the method in FIG. 5A as being performed by a processing logic, is to be regarded in an illustrative rather than a restrictive sense.

In block 502, a processing logic receives a plurality of measurements that are measured from a sensor array when the sensor array is in an unsettled state. The measurements are affected by a contact at the touch-surface of the sensor array by a conductive object (e.g., such as a stylus or user's finger). In some embodiments, the measurements received by the processing logic may include diff signal values for all (or a portion) of the sensor elements in the sensor array; in other embodiments, the processing logic may receive raw measurements (e.g., raw capacitances) from the sensor elements and may compute the corresponding diff signal values.

After receiving and/or computing the diff signals corresponding to the measurements, in block 504 the processing logic determines whether there are any remaining RX electrodes for which the diff signals need to be adjusted for tail effect. If so, the processing logic performs in turn the operations in blocks 506 to 520 on the diff signals for each remaining RX electrode. In one example the processing logic may store in memory, and perform computations on, the diff signals corresponding to the sensor elements along the RX electrode that is currently being processed, as well as the index values associated with the transmit electrodes that form these sensor elements.

In block 506, the processing logic initializes to zero a suitable memory structure (e.g., such as a variable) that is configured for storing the sum of the index values corresponding to the transmit electrodes. For example, if "SumIdx" denotes is a variable for storing the sum of the index values, the processing logic performs the initialization operation of:

$$\text{SumIdx}=0.$$

Similarly, in block 506 the processing logic initializes to zero a suitable memory structure (e.g., such as a variable) that is configured for storing the sum of the diff signals corresponding to the RX electrode that is currently being processed. For example, if "SumSig" denotes is a variable for storing the sum of diff values, the processing logic performs the initialization operation of:

$$\text{SumSig}=0.$$

In block 508, the processing logic determines whether there are any TX electrodes diff signals remaining to be processed for the current RX electrode. If so, the processing logic performs in turn the operations in block 510 to 514 for the diff signals determined at each TX electrode along the current RX electrode. For example, if "txIndex" denotes an index value for a given TX electrode, the processing logic performs the operations in blocks 510 to 514 for each txIndex value.

In block 510, the processing logic determines whether the diff value for the current TX electrode is less than a certain threshold. For example, if "rx" represents the RX index value of the RX electrode that is currently being processed and "tx" indicates the txIndex value of the current TX electrode, the processing logic performs the comparison operation of $$\text{diff}[rx,tx] < \text{THRESHOLD}$$

where "THRESHOLD" indicates a fixed (but possibly configurable) parameter value, and diff[rx,tx] represents the diff signal value determined from the sensor element at the intersection of the current RX electrode and the current TX electrode. In the example method illustrated in FIG. 5A, the threshold is used to exclude from the computations any diff signal values that may be associated with a contact that may be present at the sensor array. In some embodiments, based on experimental data it was determined that using a threshold parameter value in this manner may lead to more accurate adjustments for tail effects. It is noted that various embodiments may use different threshold values depending on the particular type of sensor array used, on the types of contacts and their characteristics that the sensor is expected to detect, as well as other embodiment-specific characteristics.

If in block 510 the processing logic determines that the diff value for the current TX electrode is not less than the threshold, the processing logic skips the operations in blocks 512 and 514 and then proceeds back to block 508 to select the next TX electrode (e.g., the next txIndex value) for processing. If in block 510 the processing logic determines that the diff value for the current TX electrode is less than the threshold, the processing logic performs the operations in block 512.

In block 512, the processing logic adds the current txIndex value to the running sum of TX index values for the current RX electrode. For example, the processing logic performs the operation new_SumIdx=SumIdx+txIndex where new_SumIdx is the new running sum of TX index values for the current RX electrode. The processing logic then proceeds to the operations in block 514.

In block 514, the processing logic adds the current diff signal value to the running sum of diff signal values for the current RX electrode. For example, the processing logic performs the operation new_SumSig=SumSig+diff[rx,tx]

where diff [rx,tx] represents the diff signal value determined from the sensor element at the intersection of the current RX electrode and the current TX electrode, and where new_SumSig is the new running sum of diff signal values for the current RX electrode. Thereafter, the processing logic proceeds back to block 508 to select the next TX electrode (e.g., the next txIndex value) for processing.

In this manner, the processing logic proceeds to perform the operations in blocks 508 to 514 for each TX electrode (e.g., each txIndex value) associated with the current RX electrode. When the processing logic determines in block 508 that there are no more TX electrodes (e.g., no more txIndex values) remaining to be processed, the processing logic proceeds with the operations in block 516. At this step in the process, the variable SumSig stores the sum of all diff signal values that need to be adjusted for tail effect along the current RX electrode, and the variable SumIdx stores the sum of the TX index values of these diff signal values.

In block 516, the processing logic determines if the sum of TX index values is different than zero. For example, the processing logic performs the operation of SumIdx< >0.

If the sum of TX index values is equal to zero, this may indicate that the diff values obtained for the sensor elements along the current RX electrode do not need to be adjusted for tail effect. This may happen, for example, when there is no contact to be detected during the scan operation that yielded the initial (un-adjusted) measurements from the sensor array or when the sensors along the current RX electrode have not been affected by a contact. (Alternatively, or in addition to, this operation may be performed to avoid division-by-zero in subsequent operations.) Thus, if in block 516 the processing logic determines that the sum of TX index values is equal to zero, the processing logic skips the operations in blocks 518 and 520, and proceeds back to block 504 to process the diff signal values from the sensor elements along the next RX electrode (e.g., the RX electrode associated with the next RX index value).

If in block 516 the processing logic determines that the sum of TX index values is not equal to zero, then the processing logic proceeds accordingly to block 518.

In block 518, the processing logic determines whether there are any TX electrodes (e.g., txIndex values) remaining for which adjustment values need to be computed. If so, the processing logic performs in turn the operations in block 520 for the diff signals determined at each TX electrode along the current RX electrode. For example, the processing logic performs the operations in block 520 for each txIndex value.

In block 520, the processing logic computes an adjusted measurement for each sensor element along the current RX electrode by using equation (7) from the simplified version of the approximation by straight line described above. For example, the processing logic computes an adjusted diff signal value (e.g., which represents the adjusted measurement) for the sensor element at the current RX index value and the current TX index value (e.g., at [rx,tx]) according to the operation $$\text{adjusted\_diff}[rx, tx] = \text{diff}[rx,tx] - \left(txIndex * \frac{SumSig}{SumIdx}\right)$$

where diff[rx,tx] represents the diff signal value measured (or obtained) from the sensor array for the sensor element at [rx,tx]. It is noted that $$\frac{SumSig}{SumIdx}$$

represents the value of parameter a as discussed above with respect to equation (7). After computing the adjusted diff signal value for the current sensor element at [rx,tx], the processing logic proceeds back to block 518 and performs the same operations for the next sensor element along the current RX electrode, e.g, such as the sensor element at [rx,(txIndex+1)].

When in block 518 the processing logic determines that the adjusted measurements for all TX electrodes (e.g., for all values of txIndex) have been computed, the processing logic proceeds back to block 504 to process the diff signal values from the sensor elements along the next RX electrode (e.g., the RX electrode having the next RX index value).

When in block 504 the processing logic determines there are no remaining RX electrodes for which the diff signals need to be adjusted for tail effect, the processing logic proceeds with the operations in block 522. At this step in the process, all the measurements (e.g., the measurements for all RX electrodes) that were received in block 502 have been processed and the corresponding adjusted measurements (which eliminate the tail effect) have been computed. Thus, in block 522 the processing logic may use the adjusted measurements for any subsequent operations or may send the adjusted measurements to another component for further processing. Examples of such subsequent processing operations include, but are not limited to, determining the location coordinates of the contact on the sensor array and/or tracking the movement of the contact on the touch-sensing surface of the array.

Figure 5B:
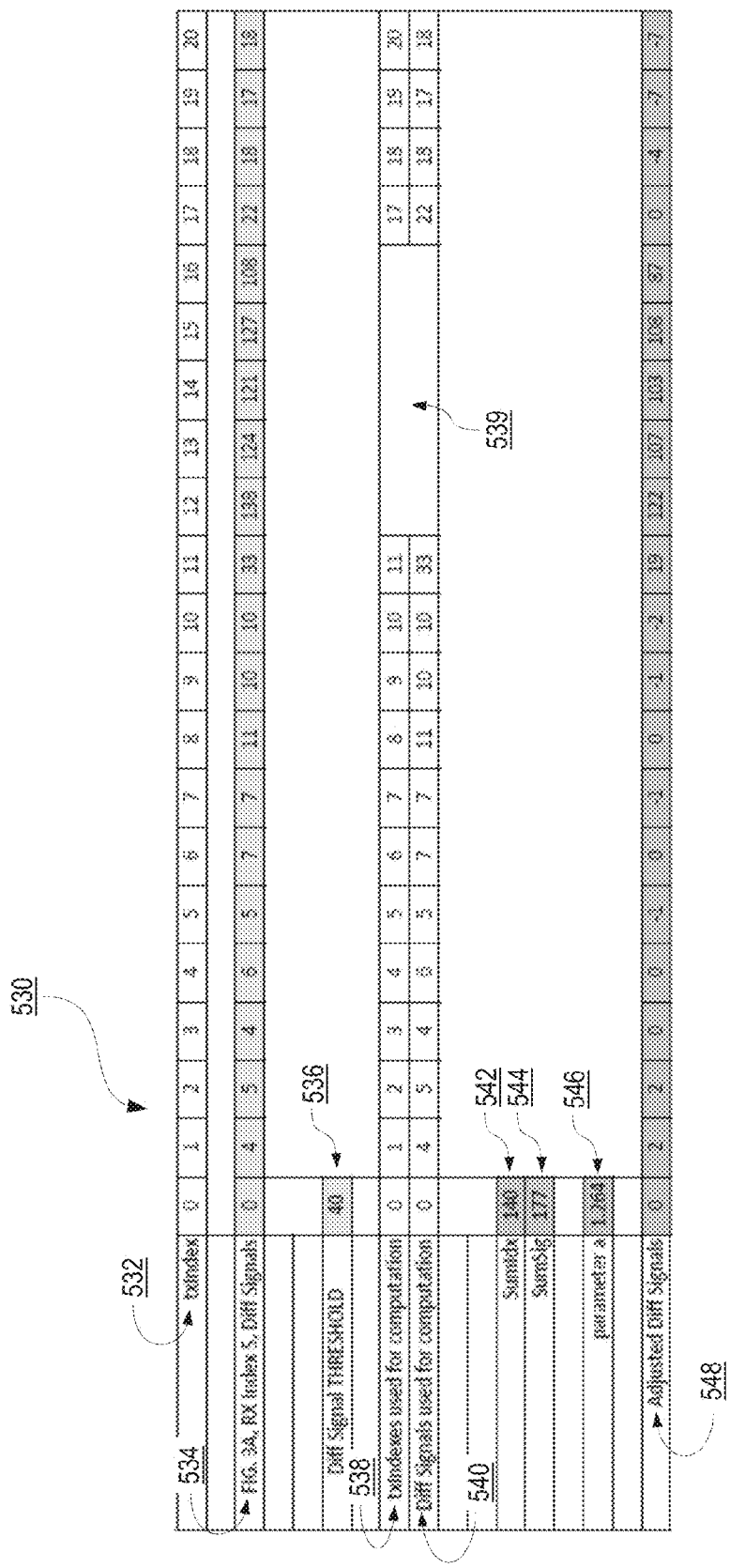
FIG. 5B is a table illustrating the inputs and the computed results for one example receive electrode according to the method of FIG. 5A.

FIG. 5B depicts table 530 that illustrates the inputs and the computed results for one example RX electrode according to the method of FIG. 5A. Specifically, table 530 illustrates the inputs and outputs of the computations performed according to blocks 506 to 520 for the diff signal values of the 5$^{th}$ RX electrode (e.g., RX index value "5") that is illustrated in FIG. 3A.

Referring to FIG. 5B, table 530 illustrates sequence 532 of txIndex values as a sequence of integers (ranging from "0" to "20") that correspond to the TX electrodes of the sensor array. Sequence 532 is used as input to the operations in blocks 506, 508, 512, 518, and 520. Sequence 534 is a sequence of the diff signal values obtained for the 5$^{th}$ RX electrode from the sensor array. Sequence 534 is used as input to the operations in blocks 510, 514, and 520. The diff signal threshold 536 that is used in this example computation is set to the value of "40". Threshold 536 is used in the comparison operation performed in block 510. Sequence 538 indicates the txIndex values that are used as input to the operations in block 512, and sequence 540 indicates the diff signal values that are used as input to the operations in block 514. As illustrated in FIG. 5B, reference numeral 539 illustrates the gaps in sequences 538 and 540 that are not used in the operations of blocks 512 and 514. The reason for these gaps is that the diff signal values corresponding thereto are larger than the threshold 536 (e.g., larger than value "40") as determined in block 510, and are therefore excluded.

In operation, a processing logic first performs the operations in block 506 to initialize to zeros the running sum 542 ("SumIdx") of txIndex values and the running sum 544 ("SumSig") of diff signal values. Then, the processing logic enters the loop of blocks 510 to 514. At each iteration, the processing logic compares the current diff signal value to threshold 536 according to block 510. If the diff signal value is greater than or equal to the threshold value of "40", the processing logic skips the operations in blocks 512 and 514 and proceeds back to block 508 to process the next diff signal value. If in block 510 the diff signal value is smaller than the threshold value of "40", the processing logic adds the current txIndex value to the running sum 542 according to operation 512, and also adds the current diff signal value to the running sum 544 of diff signal values. When all diff signal values for the RX electrode (e.g., sequence 534) have been processed, as illustrated in FIG. 5B the running sum 542 ("SumIdx") of txIndex values has the value of "140", and the running sum 544 ("SumSig") of diff signal values has the value of "177". The processing logic then exits from block 508 and proceeds to block 516.

At block 516, the processing logic determines whether the running sum 542 ("SumIdx") is different than zero. Since the running sum 542 has the value of "140", the processing logic proceeds with the loop of blocks 518 to 520 to compute sequence 548, which represents the diff signal values corresponding to sequence 534 but adjusted for tail effect. For example, according to the operations of block 520, for txIndex value of "9" the processing logic performs the computation of $$\text{adjusted\_diff}[5, 9] = 10 - \left(9 * \frac{177}{140}\right) = 10 - 11.38 = -1.38 \approx -1$$

Thus, as adjusted for tail effect, diff signal value for txIndex value of "9" is equal to "−1.38", or to "−1" as rounded to the nearest integer. (It is noted such rounding operation is performed in the computations for all values in sequence 548 that are illustrated in FIG. 5B.) In the above computation, the value of $$\frac{177}{140} = 1.264$$

represents the value 546 of parameter value a according to equation (7) above, and this value is the same in the computations of all values in sequence 548.

Experimental Results

Figure 6A:
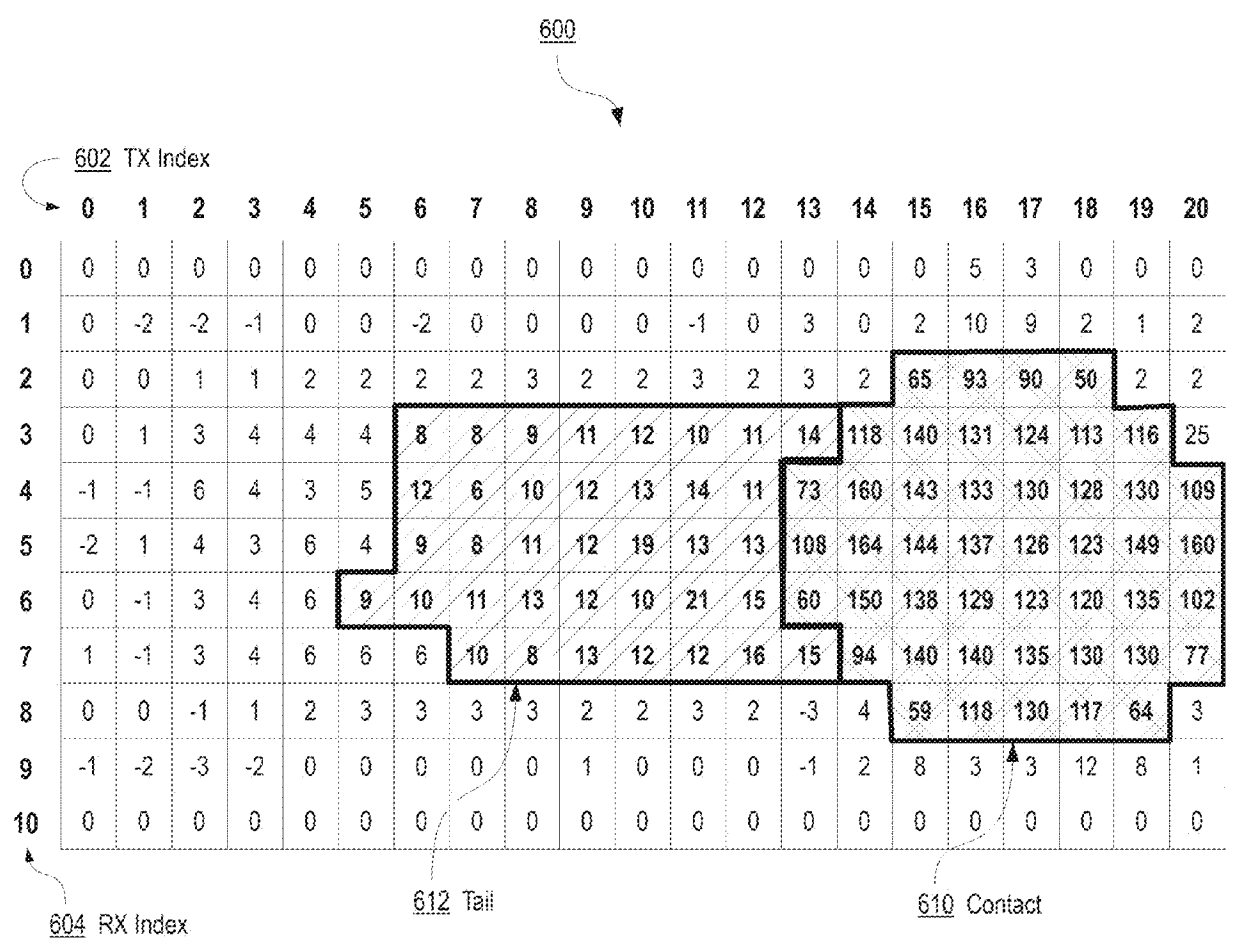

FIG. 6A is a block diagram illustrating experimental results of a tail effect according to an example embodiment. Specifically, FIG. 6A illustrates a logical diagram of a sensor array 600, where the sensor elements of the array are represented as boxes at the intersections of 21 transmit electrodes and 11 receive electrodes. The transmit electrodes are associated with the values of TX index 602, and the receive electrodes are associated with the values of RX index 604.

In FIG. 6A, the diff signal values for the sensor elements of sensor array 600 are obtained by a scan operation at a time when a robot emulates, on the touch-surface of the sensor array, a finger touch of a finger having a size of 30 mm by 35 mm. The diff signal values obtained by the scan operation indicate the presence of both contact 610 and tail 612.

FIG. 6B is a block diagram illustrating experimental results of eliminating the tail effect of FIG. 6A. Specifically, FIG. 6B shows the diff signals from sensor array 600 as they were adjusted for tail effect in accordance with the method of FIG. 5A (e.g., by using a simplified version of the approximation by straight line with a threshold value of "40" and rounding-down, e.g., a FLOOR operation, of the adjusted values to the nearest integer value towards minus infinity). As illustrated in FIG. 6B, the application of the techniques described herein has resulted in an adjusted contact 620 with the tail effect being substantially eliminated from the diff signals that were obtained by the scan operation from the sensor array.

Various embodiments of the techniques for eliminating tail effect described herein may include various operations. These operations may be performed by hardware components, software, firmware, or a combination thereof. As used herein, the term "coupled to" may mean coupled directly or indirectly through one or more intervening components. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Certain embodiments may be implemented as a computer program product that may include instructions stored on a non-transitory computer-readable medium, e.g., such as volatile storage and/or non-volatile storage. These instructions may be used to program one or more devices that include one or more general-purpose or special-purpose processors (e.g., such as Central Processing Units, or CPUs) or equivalents thereof (e.g., such as processing cores, processing engines, microcontrollers, and the like), so that when executed by the processor(s) or the equivalents thereof, the instructions cause the device(s) to perform the described operations for eliminating tail effect. A computer-readable medium may also include one or more mechanisms for storing or transmitting information in a form (e.g., software, processing application) that is readable by a machine (e.g., such as a device or a computer). The non-transitory computer-readable storage medium may include, but is not limited to, electromagnetic storage medium (e.g., floppy disks, hard disks, and the like), optical storage medium (e.g., CD-ROM), magneto-optical storage medium, read-only memory (ROM), random-access memory (RAM), erasable programmable memory (e.g., EPROM and EEPROM), flash memory, or another now-known or later-developed type of medium that is suitable for storing information.

Additionally, some embodiments may be practiced in distributed computing environments where the computer-readable medium is stored on and/or executed by more than one computer system. In addition, the information transferred between computer systems may either be pulled or pushed across the transmission medium connecting the computer systems. Although the operations of the method(s) herein are shown and described in a particular order, the order of the operations of each method may be altered so that certain operations may be performed in an inverse order or so that certain operation may be performed, at least in part, concurrently with other operations. In other embodiments, instructions or sub-operations of distinct operations may be in an intermittent and/or alternating manner.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A device comprising:
a sensor configured to obtain a plurality of measurements from a sensor array in a scan operation when the sensor array is in an unsettled state after a previous scan operation, wherein the plurality of measurements are representative of a conductive object that is proximate to a touch-sensing surface of the sensor array, and wherein the sensor array comprises a plurality of transmit electrodes and a plurality of receive electrodes; and
a processing logic coupled with the sensor, wherein the processing logic is configured at least to:
determine a set of adjustment values that correspond to a tail effect associated with the conductive object represented by the plurality of measurements;
wherein adjustment values for a particular receive electrode are computed based on a sum of indices of transmit electrodes along the particular receive electrode; and
generate adjusted measurements corresponding to the plurality of measurements based on the set of adjustment values.

2. The device of claim 1, wherein the sensor is configured to obtain the plurality of measurements based on a frequency of sensor recharging that is higher than an optimal frequency that allows the sensor array to substantially settle between measurements.

3. The device of claim 2, wherein the frequency of sensor recharging is a cause for the tail effect.

4. The device of claim 1, wherein the tail effect comprises a parasitic signal increase or a parasitic signal decrease that is extended along one or more rows or columns of sensor elements in the sensor array, rather than being localized to sensor elements directly affected by the conductive object.

5. The device of claim 1, wherein the sensor array is a capacitive sensor array and the plurality of measurements are capacitive measurements.

6. The device of claim 1, wherein the processing logic is further configured to determine location coordinates on the touch-sensing surface for the conductive object based on the adjusted measurements.

7. The device of claim 1, wherein the processing logic is further configured to track movement of the conductive object on the touch-sensing surface based on the adjusted measurements.

8. The device of claim 1, wherein the processing logic is further configured to generate subsequent adjusted measurements corresponding to a subsequent plurality of measurements responsive to a subsequent movement of the conductive object on the touch-sensing surface.

9. The device of claim 1, wherein the plurality of measurements include signal values for sensor elements formed by the particular receive electrode of the sensor array, and wherein the adjusted measurements include adjusted values corresponding to the signal values.

10. The device of claim 9, wherein in order to determine the adjusted values for the particular receive electrode, the processing logic is configured to:
compute the sum of indices of transmit electrodes that form the sensor elements along the particular receive electrode;
compute a sum of the signal values for the sensor elements along the particular receive electrode;
compute a parameter value based on the sum of indices and the sum of the signal values; and
adjust each signal value of the signal values, to obtain a corresponding adjusted value, based at least on: said each signal value, the parameter value, and an index of a corresponding transmit electrode.

11. A method comprising:
receiving a plurality of measurements from a sensor array in a scan operation when the sensor array is in an unsettled state after a previous scan operation, wherein the plurality of measurements are representative of a conductive object that is proximate to the sensor array, and wherein the sensor array comprises a plurality of transmit electrodes and a plurality of receive electrodes;
a processing device determining a set of adjustment values that correspond to a tail effect associated with the conductive object represented by the plurality of measurements;
wherein adjustment values for a particular receive electrode are computed based on a sum of indices of transmit electrodes along the particular receive electrode; and
generating adjusted measurements corresponding to the plurality of measurements based on the set of adjustment values.

12. The method of claim 11, further comprising:
periodically measuring sets of measurements from the sensor array by using a frequency of sensor recharging that is higher than an optimal frequency that allows the sensor array to substantially settle between measurements, wherein the sets of measurements include the plurality of measurements.

13. The method of claim 11, wherein a sub-optimal frequency of sensor recharging is a cause for the tail effect, and wherein the tail effect comprises a parasitic signal increase or a parasitic signal decrease that is extended along one or more rows or columns of sensor elements in the sensor array, rather than being localized to sensor elements directly affected by the conductive object.

14. The method of claim 11, further comprising determining diff signals for sensor elements of the sensor array based on the received plurality of measurements.

15. The method of claim 11, wherein:
the plurality of measurements include signal values for sensor elements formed by the particular receive electrode of the sensor array; and
the processing device determining the adjusted measurements comprises:
computing the sum of indices of transmit electrodes that form the sensor elements along the particular receive electrode;
computing a sum of the signal values for the sensor elements along the particular receive electrode;
computing a parameter value based on the sum of indices and the sum of the signal values; and
adjusting each signal value of the signal values, to obtain a corresponding adjusted measurement, based at least on: said each signal value, the parameter value, and an index of a corresponding transmit electrode.

16. The method of claim 11, further comprising one or more of:
determining location coordinates on the sensor array for the conductive object based on the adjusted measurements; and
tracking movement of the conductive object on the sensor array based on the adjusted measurements.

17. A system comprising:
a capacitive sensor array comprising a plurality of sensor elements formed by a plurality of transmit electrodes and a plurality of receive electrodes;
a capacitive sensor coupled with the capacitive sensor array, the capacitive sensor configured to measure a plurality of measurements from the plurality of sensor elements in a scan operation when the sensor array is in an unsettled state after a previous scan operation, wherein the plurality of measurements are representative of a conductive object that is proximate to the capacitive sensor array; and
a processing logic coupled with the capacitive sensor, wherein the processing logic is configured at least to:
determine a set of adjustment values that correspond to a tail effect associated with the conductive object represented by the plurality of measurements;
wherein adjustment values for a particular receive electrode are computed based on a sum of indices of transmit electrodes along the particular receive electrode; and
generate adjusted measurements corresponding to the plurality of measurements based on the set of adjustment values.

18. The system of claim 17, wherein the capacitive sensor is configured to periodically measure pluralities of measurements based on a frequency of sensor recharging that is higher than an optimal frequency that allows the plurality of sensor elements to substantially settle between measurements.

19. The system of claim 17, wherein a sub-optimal frequency of sensor recharging is a cause for the tail effect, wherein the tail effect comprises a parasitic signal increase or a parasitic signal decrease that is extended along one or more rows or columns of sensor elements in the sensor array, rather than being localized to one or more sensor elements that are directly affected by the conductive object.

20. The system of claim 17, wherein the processing logic is configured to perform one or more of:
determine location coordinates on the capacitive sensor array for the conductive object based on the adjusted measurements; and
track movement of the conductive object on the touch-sensing surface based on the adjusted measurements.

\* \* \* \* \*